United States Patent
Tan et al.

(10) Patent No.: US 8,591,624 B2
(45) Date of Patent: Nov. 26, 2013

(54) METHODS FOR PREPARING HYDROPHOBIC METAL NANOPARTICLES AND PRECURSORS USED THEREIN

(75) Inventors: Chung-Sung Tan, Hsinchu (TW); Wei-Kuo Chin, Hsinchu (TW); Hsien-Te Hsieh, Hsinchu (TW)

(73) Assignee: National Tsing Hua University (TW)

( * ) Notice: Subject to any disclaimer, the term of this patent is extended or adjusted under 35 U.S.C. 154(b) by 439 days.

(21) Appl. No.: 12/858,451

(22) Filed: Aug. 18, 2010

(65) Prior Publication Data

US 2011/0203414 A1 Aug. 25, 2011

Related U.S. Application Data

(60) Provisional application No. 61/307,886, filed on Feb. 25, 2010.

(51) Int. Cl.
*B22F 9/24* (2006.01)
*B82Y 40/00* (2011.01)

(52) U.S. Cl.
USPC .................. 75/362; 75/371; 977/896

(58) Field of Classification Search
None
See application file for complete search history.

(56) References Cited

U.S. PATENT DOCUMENTS

| | | | |
|---|---|---|---|
| 2006/0150776 A1* | 7/2006 | Nakamoto et al. | 75/710 |
| 2009/0029148 A1* | 1/2009 | Hashimoto et al. | 428/323 |
| 2009/0075815 A1* | 3/2009 | Kaneda et al. | 502/339 |
| 2009/0221418 A1* | 9/2009 | Fischer et al. | 502/155 |
| 2009/0263656 A1* | 10/2009 | Chae et al. | 428/400 |
| 2010/0117503 A1* | 5/2010 | Mizuno et al. | 313/110 |

FOREIGN PATENT DOCUMENTS

KR 2005-031706 A * 4/2005

OTHER PUBLICATIONS

Machine Translation of KR 2005-031706-A, published Apr. 6, 2005.*

* cited by examiner

*Primary Examiner* — George Wyszomierski
(74) *Attorney, Agent, or Firm* — Bacon & Thomas, PLLC

(57) ABSTRACT

Hydrophobic metal nanoparticles are prepared by reducing a metal precursor in a non-polar or low polar organic solvent with or without volume expansion by adding $CO_2$.

40 Claims, 17 Drawing Sheets

METHODS FOR PREPARING HYDROPHOBIC METAL NANOPARTICLES AND PRECURSORS USED THEREIN

CROSS-REFERENCE TO RELATED APPLICATIONS

This application claims the priority benefit of U.S. Provisional Application No. 61/307,886 filed 25 Feb. 2010.

FIELD OF THE INVENTION

The present invention is related to the fabrication of metal nanoparticles by utilizing a novel metal carboxylate compound as a metal ion source. Moreover, the present invention is also related to a method for preparing metal nanoparticles in a gas-expanded liquid (GEL).

BACKGROUND OF THE INVENTION

Silver nanoparticles (AgNPs) and other metal nanoparticles such as copper, and palladium have attracted considerable interest in many applications owing to their intrinsic size- and shape-dependent effects on antibacterial, catalytic, electronic, and optical properties. Sigma-Aldrich Inc. provides hydrophobic silver nanoparticles dispersed in hexane with two particle size distributions of 3-7 nm and 5-15 nm, respectively. The prices of both silver colloidals are about US$180 for a quantity of 25 ml. As considering the expensive prices, researchers are eager to develop a more economical technique to prepare the dispersion of hydrophobic metal nanoparticles, such as silver and palladium, in organic solvents.

The direct synthesis of silver organosol (silver nanoparticles dispersed in an organic solvent) is known to be a problem due to the poor solubility of traditional water-soluble silver salts such as silver nitrate ($AgNO_3$), silver sulfate ($Ag_2SO_4$), silver oxide ($Ag_2O$), and silver halides (AgX, X=F, Cl, Br, or I) in organic media. Similarly, the preparation of other metal nanoparticles including copper, palladium, gold, and platinum are also limited in their poor solubility of the corresponding metal salts in organic solvents. Consequently, the two-phase based methods were developed and adopted to prepare metal organosol by using phase transfer agents. Sarathy, K. V.; Raina, G.; Yadav, R. T.; Kulkarni, G. U.; Rao, C. N. R. in an article entitled "Thiol-derivatized nanocrystalline arrays of gold, silver, and platinum" *J. Phys. Chem. B* 1997, 101, 9876 describe the procedures involving the transfer of metal hydrosols (metal nanoparticles dispersed in water) into an organic solvent by using concentrated HCl as the phase transfer agent. Brust, M.; Walker, M.; Bethell, D.; Schiffrin, D. J.; Whyman, R. in an article entitled "Synthesis of thiol-derivatized gold nanoparticles in a 2-phase liquid-liquid system" *J. Chem. Soc. Chem. Commun.* 1994, 801 report the synthesis of gold nanoparticles by reducing the $AuCl^-$ ions with sodium borohydride in the water-toluene phase system. In their report, $AuCl^-$ ions was transferred from water phase into toluene phase using tetraoctylammonium bromide as the phase transfer agent. The disadvantages of aforementioned two-phase method were the necessity of toxic phase transfer agents such as concentrated HCl or tetraoctylammonium bromide, as well as the complicated synthetic process.

It is well-known that silver carboxylates with long alky chain are utilized as the silver source in the field of thermographic and photothermographic imaging techniques. In addition, the solventless approaches have been adopted to produce hydrophobic AgNPs through thermal decomposition of silver carboxylates with long alky chain under high temperature condition. For example, Abe, K.; Hanada, T.; Yoshida, Y.; Tanigaki, N.; Takiguchi, H.; Nagasawa, H.; Nakamoto, M.; Yamaguchi, T.; Yase, K. in an article entitled "Two-dimensional array of silver nanoparticles" employed the thermolysis of silver carboxylates with long alky chain (e.g., those containing 14-18 carbon atoms) to fabricate the hydrophobic silver nanoparticles at 250° C. in $N_2$ atmosphere. Similar approaches are also described in Lee, S. J.; Han, S. W.; Choi, H. J.; Kim, K. *J. Phys. Chem. B* 2002, 106, 2892 and in Yang, N. J.; Aoki, K.; Nagasawa, H. *J. Phys. Chem. B* 2004, 108, 15027. However, the forementioned silver salts of carboxylic acid with long alky chains were not suitable to serve as the silver ion sources in wet chemical synthetic process due to their low solubility in water and organic solvents. Jacobson, C. A.; Holmes, A. in an article entitled "Solubility data for various salts of lauric, myristic, palmitic, and stearic acids" *J. Biol. Chem.* 1916, 25, 29 showed the results of low solubility of silver laurate, myristate, palmitate, and stearate in various solvents including water, alcohols, and ether. In addition, Malik, W. U.; Jain, A. K.; Jhamb, O. P. in an article entitled "Solutions of soaps in organic solvents" *J. Chem. Soc. A* 1971, 1514 investigated the low solubility of silver salts of carboxylic acid in various organic solvents. Therefore, the lack of organo-soluble metal precursors is the main impediment to the preparation of hydrophobic metal nanoparticles in wet chemical synthetic process. From this viewpoint, finding organo-soluble metal precursors is a key to provide the opportunity to synthesis metal nanoparticles directly in organic media.

The nontoxic, non-flammable, inexpensive, and abundant nature of carbon dioxide ($CO_2$) has attracted great attention as an ideal processing medium in the fields of material science and nanotechnology (Eckert, C. A.; Knutson, B. L.; Debenedetti, P. G. *Nature* 1996, 383, 313; Holmes, J. D.; Lyons, D. M.; Ziegler, K. J. *Chem.-Eur J.* 2003, 9, 2144; Johnston, K. P.; Shah, P. S. *Science* 2004, 303, 482; Shah, P. S.; Hanrath, T.; Johnston, K. P.; Korgel, B. A. *J. Phys. Chem. B* 2004, 108, 9574). Metal nanoparticles, including silver and gold nanoparticles, have been synthesized through supercritical $CO_2$ (sc-$CO_2$) technologies such as the water-in-$CO_2$ (w/c) microemulsions (Ji, M.; Chen, X. Y.; Wai, C. M.; Fulton, J. L. *J. Am. Chem. Soc.* 1999, 121, 2631; Ohde, H.; Hunt, F.; Wai, C. M. *Chem. Mat.* 2001, 13, 4130; McLeod, M. C.; McHenry, R. S.; Beckman, E. J.; Roberts, C. B. *J. Phys. Chem. B* 2003, 107, 2693), rapid expansion of supercritical solution into a liquid solvent (RESOLD) (Sun, Y. P.; Atorngitjawat, P.; Meziani, M. J. *Langmuir* 2001, 17, 5707; Meziani, M. J.; Pathak, P.; Beacham, F.; Allard, L. F.; Sun, Y. P. *J. Supercrit. Fluids* 2005, 34, 91), sc-$CO_2$ flow process (McLeod, M. C.; Gale, W. F.; Roberts, C. B. *Langmuir* 2004, 20, 7078), arrested precipitation (Shah, P. S.; Husain, S.; Johnston, K. P.; Korgel, B. A. *J. Phys. Chem. B* 2001, 105, 9433; Shah, P. S.; Husain, S.; Johnston, K. P.; Korgel, B. A. *J. Phys. Chem. B* 2002, 106, 12178.), and other specific approaches (Fan, X.; McLeod, M. C.; Enick, R. M.; Roberts, C. B. *Ind. Eng. Chem. Res.* 2006, 45, 3343; Moisan, S.; Martinez, V.; Weisbecker, P.; Cansell, F.; Mecking, S.; Aymonier, C. *J. Am. Chem. Soc.* 2007, 129, 10602; Esumi, K.; Sarashina, S.; Yoshimura, T. *Langmuir* 2004, 20, 5189). However, sc-$CO_2$ is a poor solvent for many high molecular weight and polar compounds due to the low dielectric constant and polarizability per volume of $CO_2$. Accordingly, $CO_2$-philic fluorinated molecules including surfactants, capping ligands, and metal precursors are required in the prior art to enhance the solubility of compounds in sc-$CO_2$, although they are economically and environmentally unfavorable. Besides, a quite high process pressure (generally over 100 bar) is required to dissolve adequate amount of the fluorinated reagents in compressed $CO_2$.

Recently, a non-fluorinated agent having branched alky chains, isostearic acid (2,2,4,8,10,10-Hexamethylundecane-5-carboxylic acid), is successfully employed to disperse silver nanoparticles in sc$CO_2$. Bell, P. W.; Amand, M., Fan, X.; Enick, R. M.; Roberts, C. B. in an article entitled "Stable dispersions of silver nanoparticles in carbon dioxide with fluorine-free ligands" *Langmuir* 2005, 21, 11608 disclose the successful dispersion of isostearic acid-capped silver nanoparticles in high pressure (276 bar) $CO_2$ or in $CO_2$ with 10 vol % hexane as cosolvent. In their article, silver nanoparticles were synthesized within the cores of AOT reverse micelles in advance. AOT (sodium bis(2-ethylhexyl) sulfocuccinate) was utilized as the surfactant to form micelles with nanosized reaction space in aqueous medium. While silver nanoparticles were formed in the reverse micelles, isostearic acid was added to replace the AOT as the capping agent on the surface of the silver nanoparticles. Then, the authors successfully dispersed the isostearic acid-capped silver nanoparticles in compressed $CO_2$. Anand, M.; Bell, P. W.; Fan, X.; Enick, R. M.; Roberts, C. B. in an article entitled "Synthesis and steric stabilization of silver nanoparticles in neat carbon dioxide solvent using fluorine-free compounds" *J. Phys. Chem. B* 2006, 110, 14693 disclose the in-situ synthesis of silver nanoparticles in the presence of isostearic acid in compressed $CO_2$ wherein silver bis(3,5,5-trimethyl-1-hexyl) sulfosuccinate (Ag-AOT-TMH) was reduced to form silver nanoparticles at high pressure. Based on the results of two aforementioned articles, the authors suggested that the branched alky chain in isostearic acid is the key to afford the sufficient solvent-ligand interactions between silver nanoparticles and $CO_2$. Thus, silver nanoparticles were able to be stably dispersed in $CO_2$. However, the main drawback in their methods is the necessity of high pressure (207 bar) and cosolvent (cyclohexane) in order to improve the solvent strength of $CO_2$ and the dispersibility of silver nanoparticles.

Instead of using sc$CO_2$ as a reaction medium, $CO_2$-expanded liquids (CXLs) form a new class of tunable solvents for chemical syntheses. Jessop, P. G; Subramaniam, B. in an article entitled "Gas-expanded liquids" *Chem. Rev.* 2007, 107, 2666 describe CXLs are the mixtures where the compressed $CO_2$ are dissolved into organic solvents accompanying volume expansion of the solutions. As compared to sc$CO_2$, CXLs are benefited by the milder operating pressure (tens of bar). Kordikowski, A.; Schenk, A. P.; VanNielen, R. M.; Peters, C. J. in an article entitled "Volume expansions and vapor-liquid equilibria of binary mixtures of a variety of polar solvents and certain near-critical solvents" *J. Supercrit. Fluids* 1995, 8, 205 disclose the volume expansion of organic solvents was 500% higher than by dissolving $CO_2$ under mild pressure ranging from 40 to 70 bar. Therefore, the physicochemical properties of CXLs, including density, viscosity, solute diffusivity, and gas solubility can be adjusted easily by dissolving various amount of $CO_2$ into organic solvents (Yin, J. Z.; Tan, C. S. *Fluid Phase Equilib.* 2006, 242, 111; Lin, I. H.; Tan, C. S. *J. Chem. Eng. Data* 2008, 53, 1886; Lin, I. H.; Tan, C. S. *J. Supercrit. Fluids* 2008, 46, 112; Lopez-Castillo, Z. K.; Aki, S. N. V. K.; Stadtherr, M. A.; Brennecke, J. F. *Ind. Eng. Chem. Res.* 2008, 47, 570; Xie, Z. Z.; Snavely, W. K.; Scurto, A. M.; Subramaniam, B. *J. Chem. Eng. Data* 2009, 54, 1633). Moreover, Tan's group showed that the diffusivity of solutes as well as $H_2$ solubility could be enhanced in CXLs. (Yin, J. Z.; Tan, C. S. *Fluid Phase Equilib.* 2006, 242, 111; Lin, I. H.; Tan, C. S. *J. Chem. Eng. Data* 2008, 53, 1886; Lin, I. H.; Tan, C. S. *J. Supercrit. Fluids* 2008, 46, 112). Bogel-Lukasik, E.; Fonseca, I.; Bogel-Lukasik, R.; Tarasenko, Y. A.; da Ponte, M. N.; Paiva, A.; Brunner, G. in an article entitled "Phase equilibrium-driven selective hydrogenation of limonene in high-pressure carbon dioxide" reported that the hydrogenation rate of limonene in CXLs became faster compared to the pure $H_2$ system without adding $CO_2$. Therefore, the decrease of solution viscosity, increase of solute diffusivity, and higher $H_2$ solubility are beneficial to improve the mass transport as well as chemical syntheses in CXLs. On the other hand, dissolving $CO_2$ can weaken the solvating power of solvents and the precipitation of solutes is triggered in CXLs. Based on these phenomena, various methods such as gas antisolvent precipitation (GAS), precipitation with compressed antisolvent (PCA), supercritical antisolvent (SAS), solution enhanced dispersion by supercritical fluids (SEDS), and depressurization of an expanded liquid organic solution (DELOS) were adopted to precipitate fine particles composed of inorganic compounds, organic compounds, explosives, pharmaceuticals, and polymers (Jung, J.; Perrut, M. *J. Supercrit. Fluids* 2001, 20, 179; Shariati, A.; Peters, C. J. *Curr Opin. Solid State Mat. Sci.* 2003, 7, 371; Yeo, S. D.; Kiran, E. *J. Supercrit. Fluids* 2005, 34, 287). Recently, the deposition process of ligand-capped metal nanoparticles is applied to accomplish the uniform wide-area nanoparticle films and size-selection fractionation in CXLs (McLeod, M. C.; Anand, M.; Kitchens, C. L.; Roberts, C. B. *Nano Lett.* 2005, 5, 461; McLeod, M. C.; Kitchens, C. L.; Roberts, C. B. *Langmuir* 2005, 21, 2414; U.S. Pat. No. 7,384,879). In spite of these various merits in the field of material science and nanotechnology, however, applying CXLs as process medium to synthesize hydrophobic metal nanoparticles such as silver and palladium have not been reported to date. In order to take advantage of CXLs, an organo-soluble and fluorine-free metal precursor is also required to provide metal ions in organic medium.

SUMMARY OF THE INVENTION

A primary objective of the present invention is to provide an alternative technique to synthesis hydrophobic metal nanoparticles free of the drawbacks in the prior arts.

In order to achieve the objective of present invention a novel metal precursor is synthesized and employed as a metal ion source in an organic phase. In this invention, said novel metal precursor containing methylated branch alky chains was synthesized and found to have good solubility in nonpolar organic solvents and low polar organic solvents. Thus, said novel metal precursor is the feasible candidate for the synthesis of metal nanoparticles in a wet chemical synthetic process. As the reduction reaction is undergoing, the metal precursor will be decomposed into zero-valent metal as well as a free ligand, and thus the resulting ligand-capped metal nanoparticles are hydrophobic and well-dispersed in a nonpolar solvent or a low polar organic solvent.

A method for forming metal nanoparticles according to the present invention comprises reducing an organometallic compound having a formula of $(R^1R^2CHCOO)_xM$ in an organic solvent, wherein x=1 or 2; M is Ag, or Pd; $R^1$ and $R^2$ independently are C1-C22 linear or branched alkyl having a tertiary butyl group, or $R^1$ and $R^2$ together form a C2-C22 cycloalkyl having a tertiary butyl group.

Preferably, the organic solvent is expanded with a pressurized inert fluid, such as $CO_2$, $N_2O$, He, Ne, Ar, Kr, Xe, Rn, $SF_6$, $CHF_3$, $CH_2F_2$, $CH_4$, $CH_4O$, $C_2H_4$, $C_2H_6$, $(CH_3)_2O$, $(CH_2NH_2)_2$, $C_3H_6$, $C_3H_8$, $C_4H_{10}$, $C_5H_{12}$, $C_6H_6$, or $C_6H_{14}$.

More preferably, the organic solvent is a non-polar organic solvent or a low polar organic solvent having a polarity less than methanol.

Preferably, the organic solvent is C4-C12 hydrocarbon, chloroform, or terahydrofuran.

Preferably, the organic solvent is heptane, cycloheptane, hexane, cyclohexane, toluene, xylene or a mixture thereof.

Preferably, M is Ag and x=1, or M is Pd and x=2. More preferably, M is Ag and x=1.

Preferably, $R^1$ and $R^2$ independently are C3-C10 linear or branched alkyl having a terminal tertiary butyl group. More preferably, the $(R^1R^2CHCOO)_xM$ is a metal isostearate (metal salts of 2,2,4,8,10,10-Hexamethylundecane-5-carboxylic acid).

Preferably, the metal precursor is reduced in an atmosphere of a reducing agent. More preferably, the reducing agent is hydrogen, and a pressure of the atmosphere is 1 bar or higher.

Preferably, the metal precursor is reduced in an atmosphere containing a reducing agent and $CO_2$, where $CO_2$ is used to expand the organic solvent. More preferably, the reducing agent is hydrogen; a total pressure of atmosphere is 1.1-275 bar or higher, and the hydrogen has a partial pressure of 1-55 bar or higher.

Preferably, the metal precursor is reduced in the presence of a reducing agent soluble in the organic solvent. More preferably, the reducing agent is hydrazine, formaldehyde, sodium borohydride, dimethylformamide, β-D-glucose, ethylene glycol, sodium citrate, ascorbic acid, dimethyl sulfoxide, potassium bitartrate, methanol, ethanol, propan-1-ol, propan-2-ol, pyridine or poly(ethylene glycol), tris(trimethylsiloxy)silane.

Preferably, the metal precursor is reduced in the presence of a reducing agent soluble in a mixed solvent of said organic solvent and an additional solvent. More preferably, the additional solvent is acetone, methanol, ethanol, N-methyl-2-pyrrolidone, N,N-dimethylacetamide, N,N-dimethylformamide, dimethylsulfoxide, m-cresol, pyridine, acetonitrile or 2-methoxyethanol. More preferably, the method of the present invention further comprises dissolving the reducing agent in the additional solvent; dissolving the metal precursor in the organic solvent; and mixing the resulting solutions of the reducing agent and the metal precursor.

Preferably, the metal precursor is dissolved in the organic solvent with a concentration of 0.1-500 mM.

Preferably, an additional capping agent is added and dissolved in the organic solvent, and said additional capping agent is butylamine, sec-butylamine, isobutylamine, tert-butylamine, 3-methoxypropylamine, (2-methylbutyl)amine, 1,2-dimethylpropylamine, 1-ethylpropylamine, 2-aminopentane, amylamine, isopentylamine, pentylamine, tert-amylamine, 3-ethoxypropylamine, 3,3-dimethylbutylamine, hexylamine, 3-isopropoxypropylamine, heptylamine, 2-heptylamine, 1,4-dimethylpentylamine, 1,5-dimethylhexylamine, 1-methylheptylamine, 2-ethyl-1-hexylamine, octylamine, 1,1,3,3-tetramethylbutylamine, nonylamine, decylamine, dodecylamine, tridecylamine, tetradecylamine, hexadecylamine, oleylamine, octadecylamine, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, nonadecanoic acid, arachidic acid, heneicosanoic acid, behenic acid, tricosanoic acid, lignoceric acid, pamoic acid, hexacosanoic acid, 8-methylnonanoic acid, 11-methyllauric acid, 12-methyltridecanoic acid, 12-methyltetradecanoic acid, 13-Methylmyristic acid, iso-palmitic acid, 14-methylhexadecanoic acid, 15-methylpalmitic acid, 16-methylheptadecanoic acid, 17-methylstearic acid, 18-methylnonadecanoic acid, phytanic acid, 19-methylarachidic acid, or isostearic acid (2,2,4,8,10,10-Hexamethylundecane-5-carboxylic acid). More preferably, the additional capping agent is dissolved in the organic solvent with a concentration of 0.1-5000 mM.

The present invention also provides silver isostearate (silver salt of 2,2,4,8,10,10-Hexamethylundecane-5-carboxylic acid) as a precursor for the fabrication of hydrophobic silver nanoparticles.

The present invention further provides palladium isostearate (palladium salt of 2,2,4,8,10,10-Hexamethylundecane-5-carboxylic acid) as a precursor for the fabrication of hydrophobic palladium nanoparticles.

DETAILED DESCRIPTION OF THE INVENTION

Figure 1:
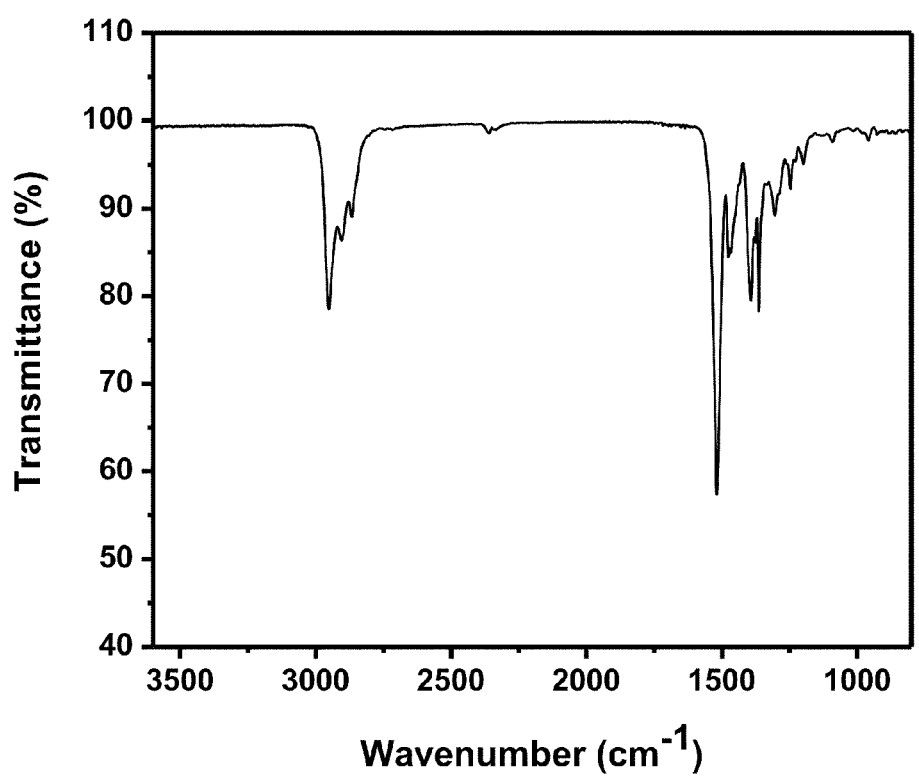
FIG. 1 shows the ATR-FTIR spectrum of silver isostearate (AgISt) prepared in Example 1 of the present invention.

The present invention synthesizes a metal precursor by preparing a mixture of carboxylic acid, alkali metal hydroxides, and water; preparing a mixture of metal salt (providing $Ag^+$, or $Pd^{2+}$ ions) and water; and mixing the two mixtures at a temperature of 40-100° C. to form $Ag^+$, or $Pd^{2+}$ salts of carboxylic acid as the metal precursor.

Hydrophobic metal nanoparticles are prepared by reducing a metal precursor dissolved in a non-polar solvent or in a low polar organic solvent (with or without volume expansion by adding $CO_2$).

According to one aspect of the present invention, the metal precursor of the present invention is reduced in a non-polar solvent or a low polar organic solvent with a reducing agent which is also soluble in the non-polar solvent or low polar organic solvent.

According to another aspect of the present invention, a solution of the metal precursor and a solution of a reducing agent are prepared separately by using independently a non-polar solvent or a low polar organic solvent. While the precursor/solvent and reducing agent/solvent solutions are mixed, the metal precursor is reduced by the reducing agent to form hydrophobic metal nanoparticles.

According to still another aspect of the present invention, the metal precursor of the present invention is reduced in a non-polar solvent or a low polar organic solvent expanded by pressurized $CO_2$, wherein a reducing agent is dissolved in the $CO_2$-expanded solvent.

According to a further aspect of the present invention, the metal precursor of the present invention is reduced to form hydrophobic metal nanoparticles in a non-polar solvent or a low polar organic solvent using hydrogen as a reducing agent.

The present invention will be better understood through the following examples which are merely illustrative and not for limiting the scope of the present invention.

EXAMPLE 1

Synthesis of Silver Isostearate (AgISt)

Silver nitrate (99%, Showa), sodium hydroxide (97%, Sigma-Aldrich), isostearic acid (2,2,4,8,10,10-hexamethylundecane-5-carboxylic acid, 95%, TCI), and heptane (99%, Echo Chemical) were used as received without further purification. Triply-distilled water (resistivity greater than 18 M cm) was produced by Millipore Milli-Q system. Carbon dioxide (99.5%) and hydrogen (99.98%) were purchased from Taiwan San Fu Gases Ltd.

AgISt was synthesized by the cation exchange reaction of sodium salt of isostearic acid and silver nitrate. 2.85 g of isostearic acid (10 mmol), 0.4 g of sodium hydroxide (10 mmol), and 100 ml triply-distilled water were well mixed at 70° C. for 30 min, then a clear solution containing sodium isostearate was formed. To this sodium isostearate solution, 100 ml of aqueous solution of silver nitrate (1.7 g, 10 mmol) was added dropwise. The yielded AgISt powders were collected, washed, and then dried under reduced pressure at 40° C. for 24 h.

Characterizations of AgISt

X-ray diffraction (XRD) pattern was recorded by a Rigaku Ultima IV X-ray diffractometer using Cu Kα radiation operated at 40 kV and 20 mA. The 2θ angle was measured from 4° to 20° with a resolution of 0.05°. The differential scanning calorimeter (DSC, TA Instrument 2010) and the thermogravimetric analyzer (TGA, Perkin-Elmer TGA7) were used to evaluate the thermal properties of samples at a heating rate of 10° C./min under $N_2$ atmosphere. The attenuated total reflection Fourier transform infrared (ATR-FTIR) spectrum was performed by Perkin-Elmer Spectrum RXI FTIR spectrometer with 2 $cm^{-1}$ resolution and 64 scans.

Results

Figure 2:
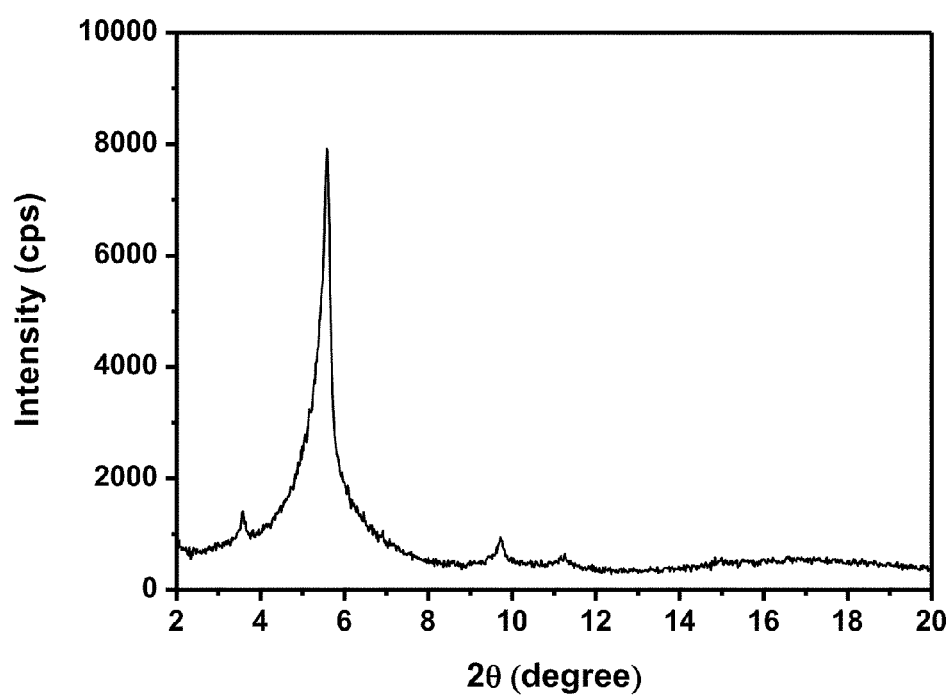
FIG. 2 shows the X-ray diffraction (XRD) pattern of the AgISt prepared in Example 1 of the present invention.
Figure 3:
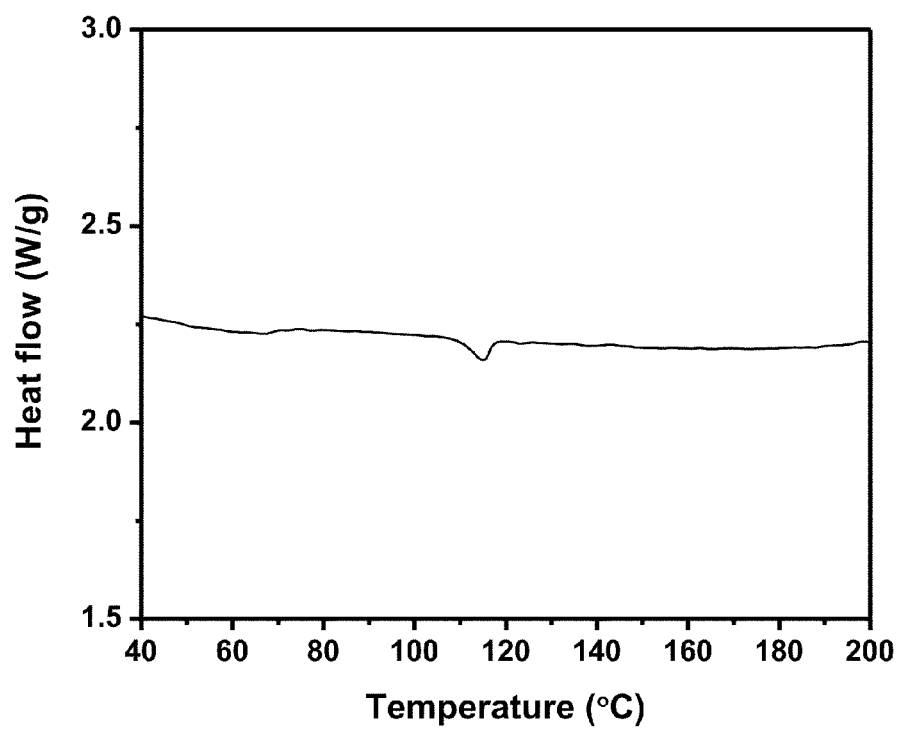
FIG. 3 shows the result of the DSC analysis of the AgISt prepared in Example 1 of the present invention.
Figure 4:
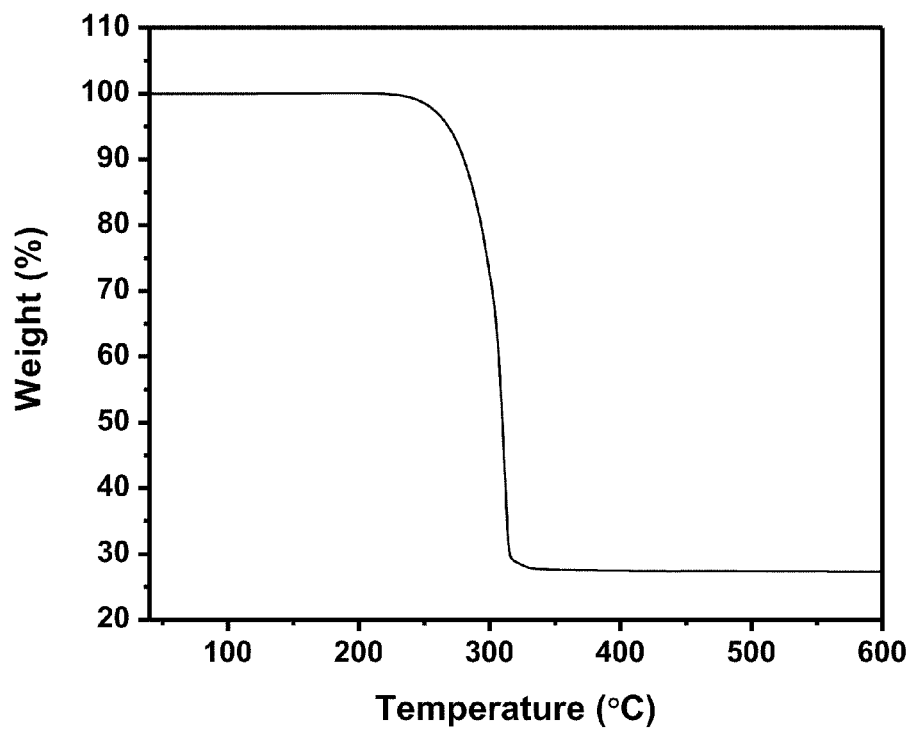
FIG. 4 shows the result of thermogravimetric analysis (TGA) of the AgISt prepared in Example 1 of the present invention.

FIG. 1 shows a FTIR spectrum of AgISt prepared above, wherein both asymmetric ($v_{as}(COO^-)$) and symmetric stretching ($v_s(COO^-)$) bands of the silver carboxylate group in AgISt appear at 1519 and 1393 $cm^{-1}$, respectively. The XRD pattern of the AgISt prepared above shows only one major reflection, indexed as (030) plane, which can be seen in FIG. 2. FIG. 3 shows the result of the DSC analysis of the AgISt prepared above, which exhibits an extremely weak endothermic transition at 116° C. (ΔH=3 J/g). The result of TGA is shown in FIG. 4. The residual mass fractions of AgISt at 800° C. is 28.3 wt %, which is slightly higher than the mass fraction of metallic silver in $C_{18}H_{35}O_2Ag$ (27.6 wt %). Lee, S. J.; Han, S. W.; Choi, H. J.; Kim, K. in an article entitled "Structure and thermal behavior of a layered silver carboxylate" *J. Phys. Chem. B* 2002, 106, 2892. showed the XRD patterns of silver stearate (AgSt), which have long alky chain, exists a set of well-defined diffraction peaks, indexed as (030), (040), (050), (060), (070), (080), (090) planes. It is well known that solid-state AgSt is an eight-membered-ring dimer composed of two $Ag^+$ ions bridged by two bidentate carboxylate groups of the stearate molecules (Tolochko, B. P.; Chernov, S. V.; Nikitenko, S. G; Whitcomb, D. R. *Nucl. Instrum. Methods Phys. Res. Sect. A-Accel. Spectrom. Dect. Assoc. Equip.* 1998, 405, 428; Binnemans, K.; Van Deun, R.; Thijs, B.; Vanwelkenhuysen, I.; Geuens, I. *Chem. Mat.* 2004, 16, 2021). The dimers are stacked orderly one next to another through the intermolecular interactions of Ag—O bonds, and the straight long alky chains in AgSt are regularly extended to grow the preferred crystal-like layered structure (Lin, B.; Dong, J. S.; Whitcomb, D. R.; McCormick, A. V.; Davis, H. T. *Langmuir* 2004, 20, 9069; Dong, J. S.; Whitcomb, D. R.; McCormick, A. V.; Davis, H. T. *Langmuir* 2007, 23, 7963) resulting in a set of well-defined peaks in the XRD diffraction. In addition, the strong Ag—O bonds between dimers and the perfect layered structure lead to the poor solubility of AgSt in solvents. In this invention, however, AgISt showed only one major reflection, indexed as (030) plane. In addition, an AgISt dimer consists of four asymmetrical methylated branched alky chains. These branched chains not only exhibit steric barriers to the Ag—O bonding between AgISt dimers but also inhibit the formation of regular layered crystal in AgISt. Hence, AgISt was found soluble in various non-polar solvents including hexane, heptanes, toluene, and xylene. Lee, S. J.; Han, S. W.; Choi, H. J.; Kim, K. in an article entitled "Structure and thermal behavior of a layered silver carboxylate" *J. Phys. Chem. B* 2002, 106, 2892. also showed two obvious endothermic peaks were found in the DSC of AgSt. In this invention, however, only an extremely weak endothermic peak was found in the DSC of AgISt. As compared with AgSt, the results of XRD and DSC show clear evidence of higher solubility of AgISt with branched alky chain than that of AgSt with long alky chain.

Synthesis of Hydrophobic Silver Nanoparticles (AgNPs)

A 50 ml glass vial containing AgISt/heptane solution (0.25 mM, 20 ml) was placed into a 150 ml stainless steel reactor. At 40° C., the reactor was filled with $H_2$ to 7 bar, followed by adding $CO_2$ to build up the total pressure of 55 bar. Through the reduction reaction, AgNPs were formed in $CO_2$-expanded heptane. Finally, a clear yellowish silver organosol was obtained by the depressurization of $H_2/CO_2$. Instead of using $CO_2$-expanded heptane, AgNPs were also synthesized in heptane in the presence of pure $H_2$ under the pressures of 7 and 55 bar, respectively.

Characterizations of AgNPs

UV-visible spectrum was obtained using a Carry 50 Conc spectrophotometer in the range of 280-800 nm, with a resolution of 2 nm. TEM image was performed on a JEOL JEM- 2100 (HT) transmission electron microscope at 200 kV after placing a drop of silver organosol on a 200 mesh carbon-coated copper grid. ImageJ software was used to analyze the size distribution and average diameter of AgNPs. The attenuated total reflection Fourier transform infrared (ATR-FTIR) spectrum was performed by Perkin-Elmer Spectrum RXI FTIR spectrometer with 2 $cm^{-1}$ resolution and 64 scans. The silver organosol was dried under reduced pressure at 40° C. to remove heptane and the resulting black precipitate was used as the sample to examine.

Results and Discussion

Figure 5A:
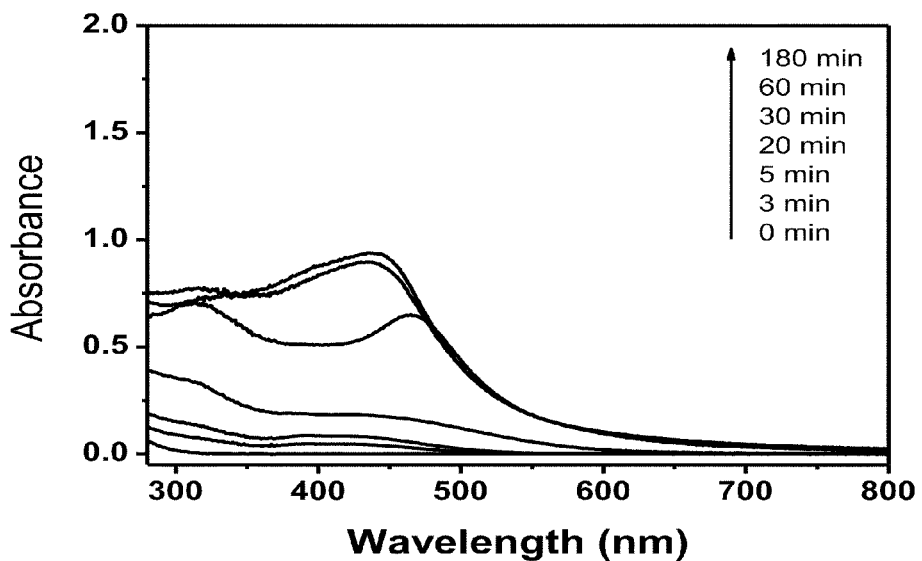
FIGS. 5a and 5b show the evolution of UV-visible absorption spectra of (a) AgNPs-a ($P_{H2}$=7 bar) and (b) AgNPs-b ($P_{H2}$=55 bar) prepared in Example 1 of the present invention, respectively.
Figure 5B:
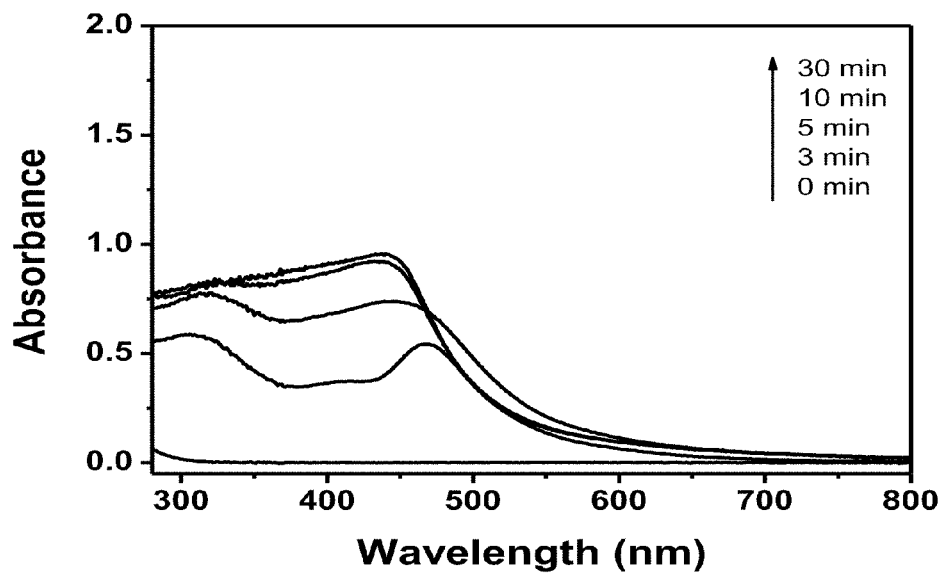
Figure 6A:
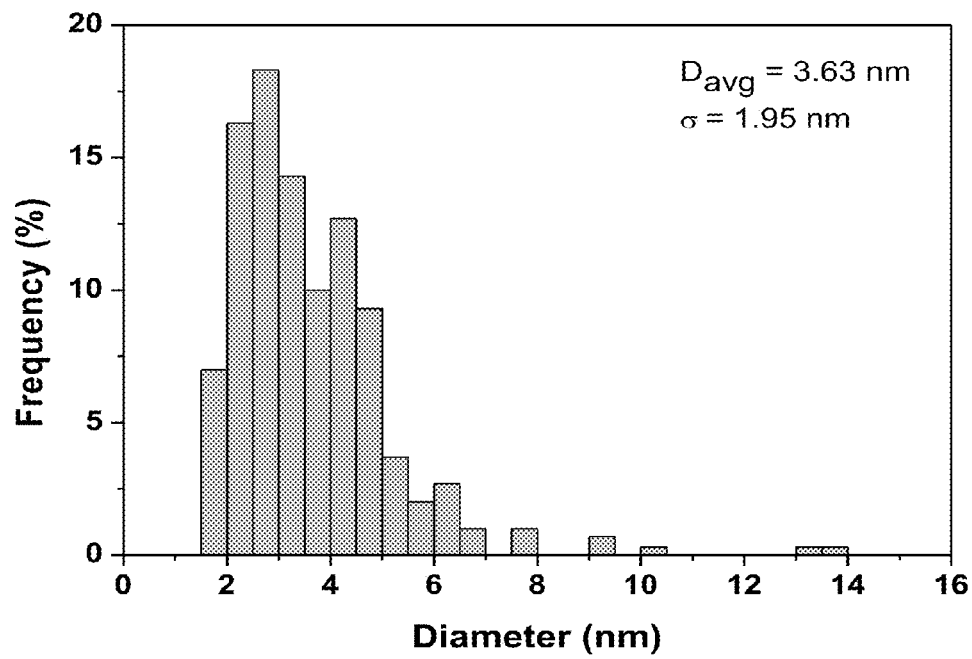
FIGS. 6a and 6b show TEM image and corresponding particle size distribution histogram of (a) AgNPs-a and (b) AgNPs-b prepared in Example 1 of the present invention, respectively. The scale bar represents 20 nm.
Figure 6A:
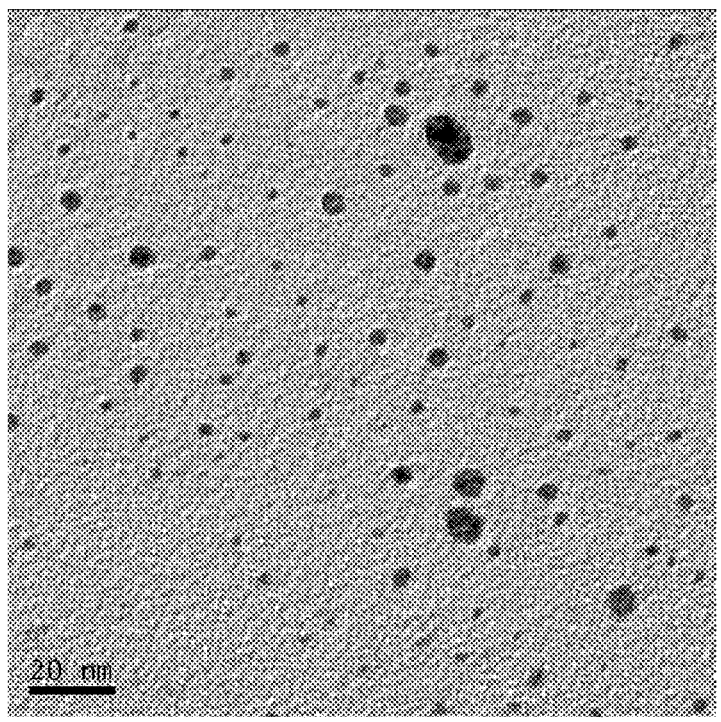
Figure 6B:
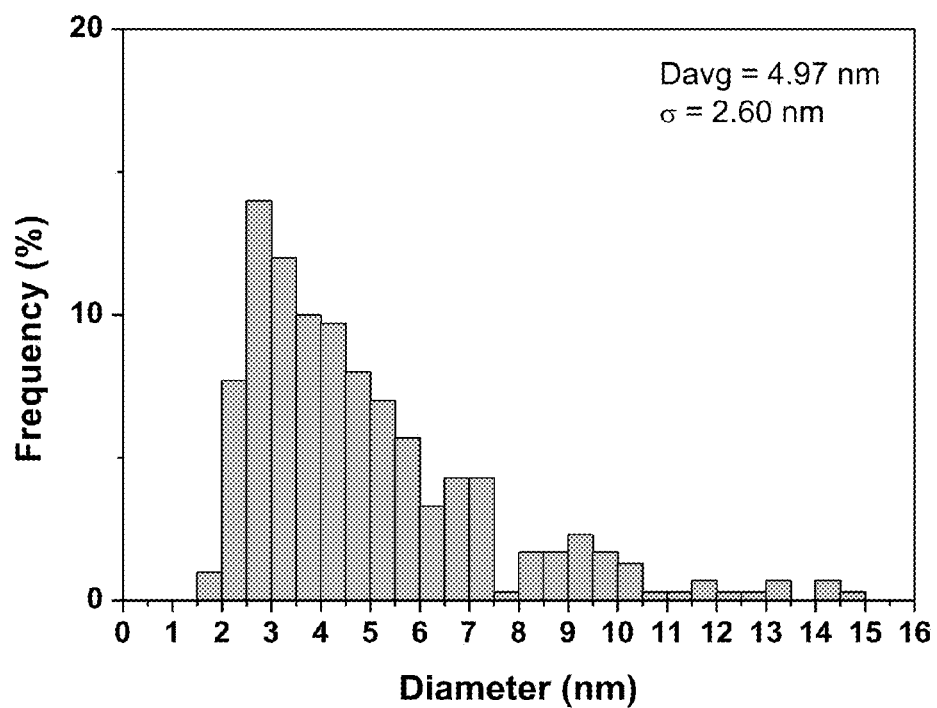
Figure 6B:
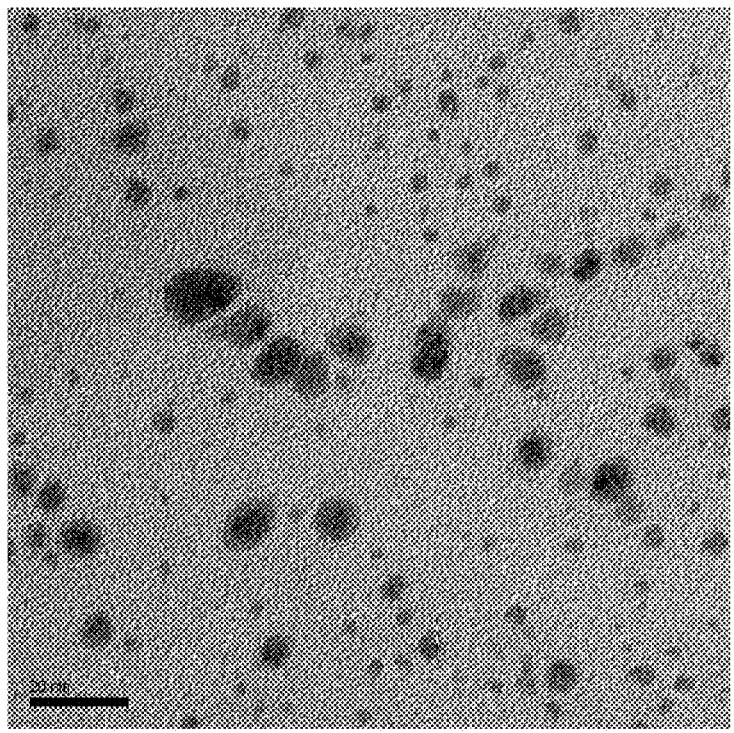

In this example, the chemical reduction method was employed to synthesize AgNPs using AgISt and $H_2$ as the precursor and reducing agent, respectively. FIGS. 5a and 5b show the evolutions of UV-visible absorption of AgNPs-a ($P_{H2}$=7 bar) and AgNPs-b ($P_{H2}$=55 bar) in the range of 280 to 800 nm. By increasing the pressure of $H_2$ from 7 to 55 bar, the rate of reduction reaction to form AgNPs was significantly increased. The maximum absorbance value, $\lambda$max, of AgNPs-a and AgNPs-b were appeared at 435 and 440 nm while the reduction times were 60 and 10 min, respectively. Further increase the reduction time, no obvious changes in the absorbance of AgNPs were observed. TEM images and the corresponding particle size distribution histograms of AgNPs-a and AgNPs-b are shown in FIGS. 6a and 6b. In TEM images, the broad size distribution of AgNPs is found. By counting 300 particles to estimate the average particle size, the average diameters of AgNPs-a and AgNPs-b were 3.63±1.95 and 4.97±2.60 nm, respectively.

Figure 7:
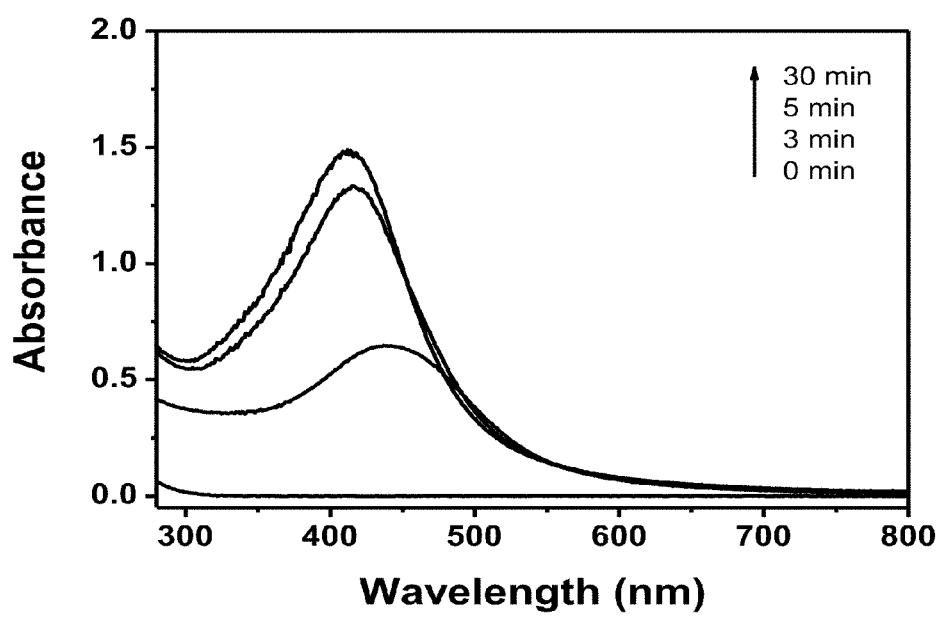
FIG. 7 shows the evolution of UV-visible absorption spectra of AgNPs synthesized in $CO_2$-expanded heptane according to Example 1 of the present invention.
Figure 8A:
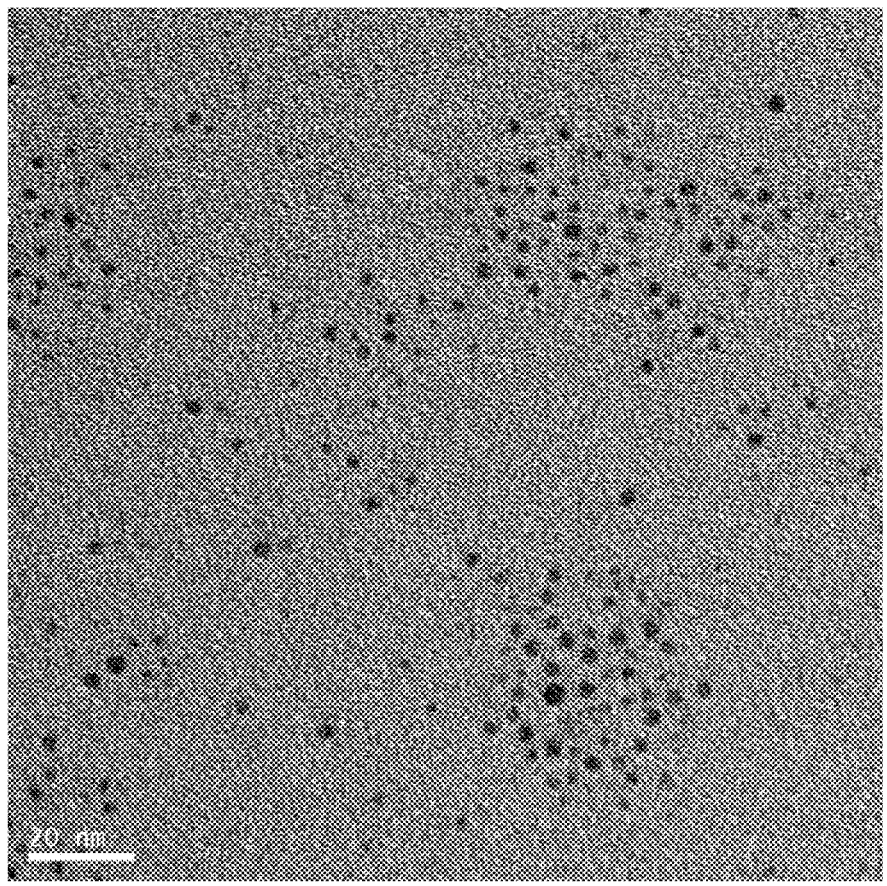
FIGS. 8a, 8b and 8c show (a) TEM image, (b) SAED pattern, and (c) corresponding particle size distribution histogram of the AgNPs synthesized in $CO_2$-expanded heptane according to Example 1 of the present invention. The scale bar represents 20 nm.
Figure 8B:
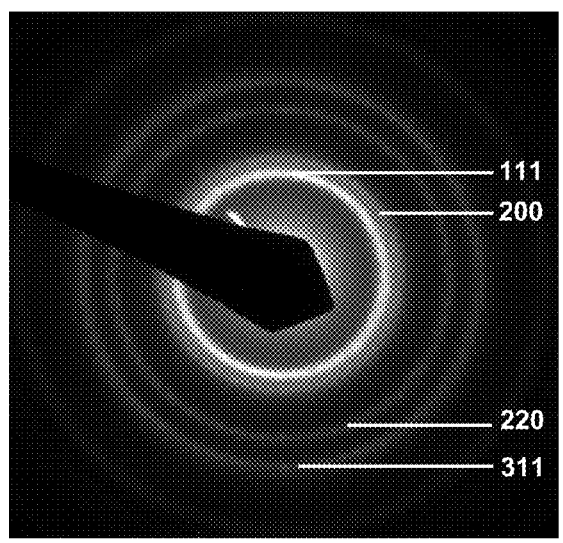
Figure 8C:
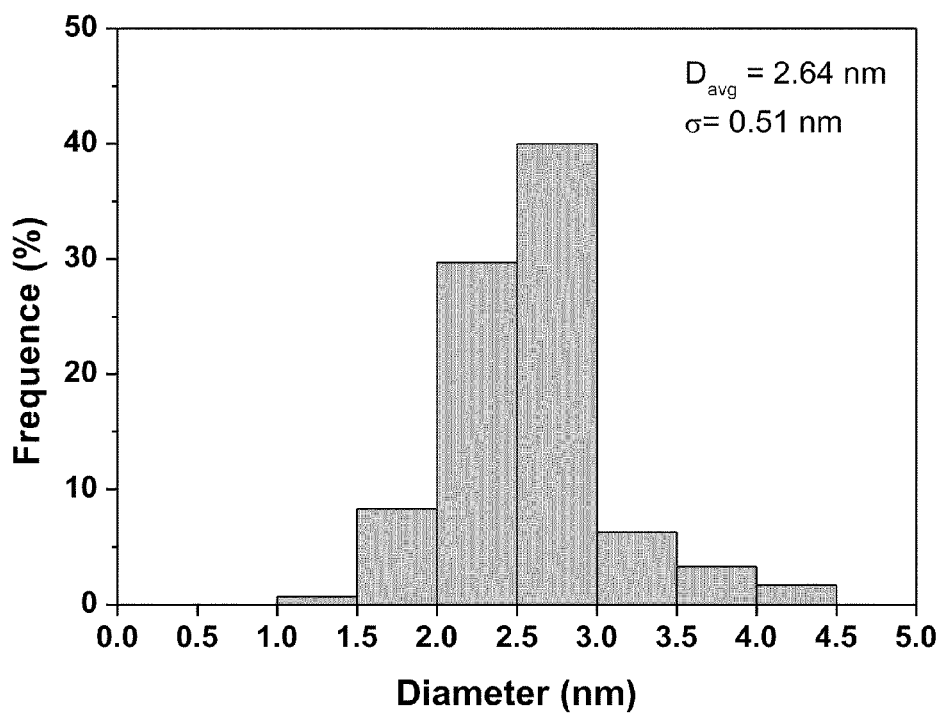

In order to enhance the reaction rate as well as narrow the particle size distribution, compressed $CO_2$ was employed to expand the AgISt/heptane solution and the effect of CXLs on the synthesis of AgNPs was investigated. FIG. 7 shows the evolution of UV-visible absorption spectra of AgNPs that were synthesized in $CO_2$-expanded heptane with $H_2$ at 7 bar, followed by adding $CO_2$ to build up the total pressure of 55 bar. While the reduction time was 3 min, a broad absorption band with $\lambda$max at 437 nm was observed. As the reduction time progressed to 30 min, the $\lambda$max was blue-shifted to 412 nm and the symmetric intense absorbance was interpreted as the surface plasmon resonance of AgNPs. Further increase the reduction time, no obvious change in the absorbance of AgNPs was found. This result indicates the efficient formation of AgNPs in $CO_2$-expanded heptane. We attributed the efficient formation of AgNPs to the enhanced mass transport of AgISt precursor and $H_2$ in $CO_2$-expanded heptane. The appearances of AgISt/heptane solution and the resulting silver organosol were also observed (not shown in the drawings), wherein the AgISt/heptane solution is colorless transparent and the resulting silver organosol becomes clear yellowish, indicating that AgNPs were well dispersed in heptane. The TEM image and particle size distribution histogram of AgNPs are illustrated in FIGS. 8a and 8c. Uniform particles were synthesized in $CO_2$-expanded heptane and the average diameter of particle was 2.64±0.51 nm. In comparing with AgNPs-a and AgNPs-b, AgNPs synthesized in $CO_2$-expanded heptane had narrow size distribution. In FIG. 8b, the selected area electron diffraction (SAED) pattern demonstrated the four rings of (111), (200), (220), and (311) crystalline planes formed in AgNPs, which indicated the typical face-centered cubic (fcc) structure in metallic silver.

Figure 9:
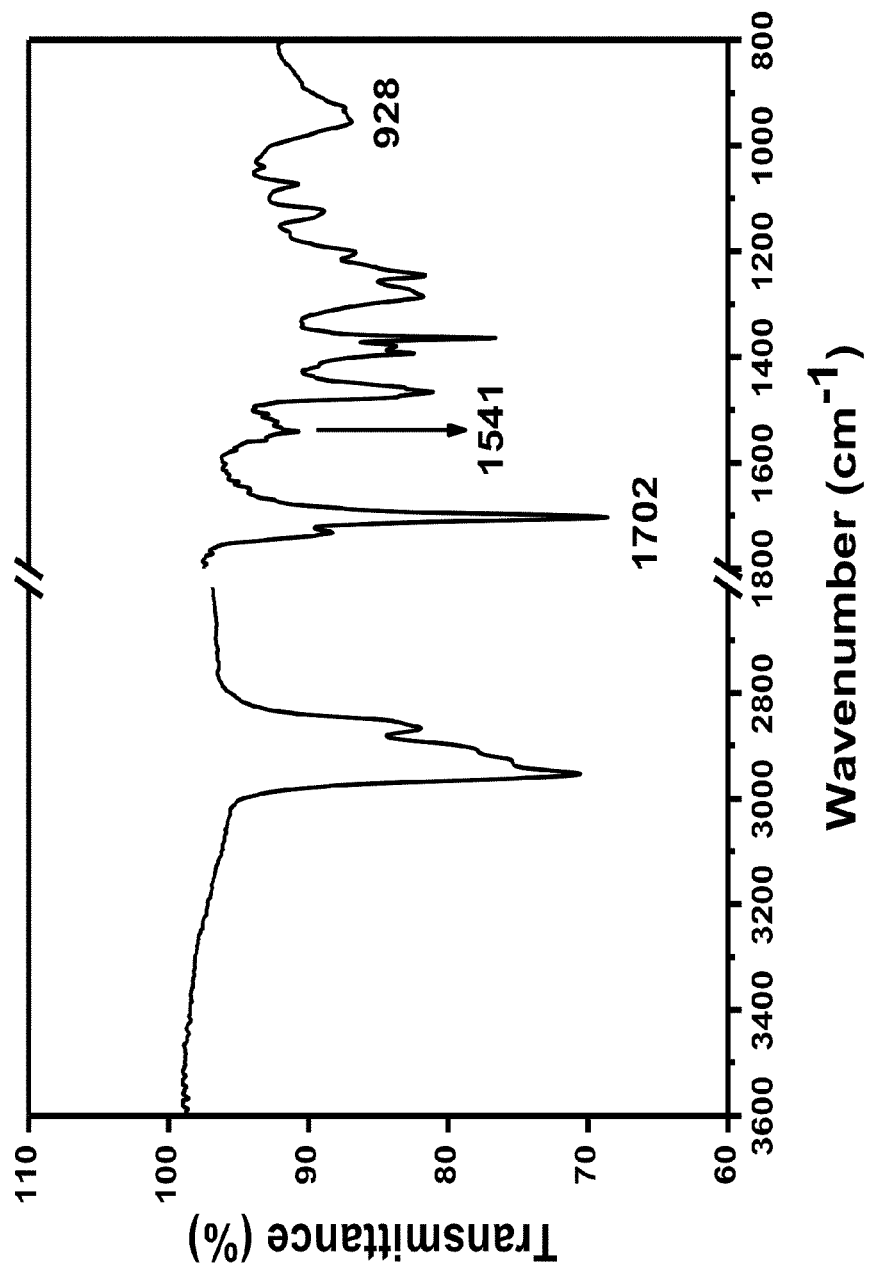
FIG. 9 shows ATR-FTIR spectrum of AgNPs synthesized in $CO_2$-expanded heptane according to Example 1 of the present invention.

The attenuated total reflection Fourier transform infrared (ATR-FTIR) spectra of AgNPs is shown FIG. 9. The stretching bands at 1702 and 928 $cm^{-1}$ were observed again due to the presence of the produced isostearic acid. Furthermore, the asymmetric ($v_{as}(COO^-)$) stretching was shifted to 1541 $cm^{-1}$, indicating that the carboxylate groups of the produced isostearic acid were capped on the surface of AgNPs. Because of high surface area-to-volume ratio, the surfaces of naked nanoparticles possess a large free energy leading to the tendency of aggregation. The adsorption of isostearic acid on AgNPs not only provided the steric repulsion to limit the growth of particle size but also exhibited solvent-ligand interactions to disperse the AgNPs in $CO_2$-expanded heptane without precipitation or aggregation. By contrast, the common ligand capped metal nanoparticles, such as dodecanethiol-capped silver and gold nanoparticles, were deposited from CXLs because of the insufficient solvation strength of thiol molecules to overcome the interparticle attraction. Hence, the synthesized AgNPs had small size of 2.64 nm and were well dispersed in heptane. Herein, the present invention first demonstrated the direct synthesis of metal nanoparticles using CXLs as a reaction medium.

EXAMPLE 2

Figure 10A:
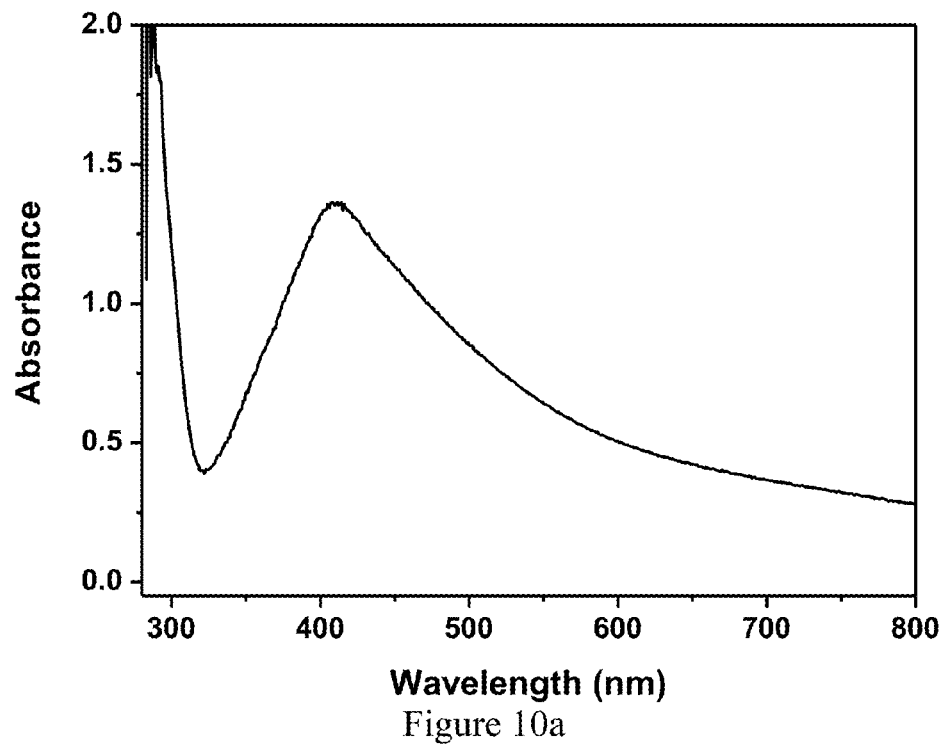
FIGS. 10a and 10b show the UV-visible spectrum and TEM image of as-prepared silver organosol using hydrazine monohydrate as the reducing agent in Example 2.
Figure 10B:
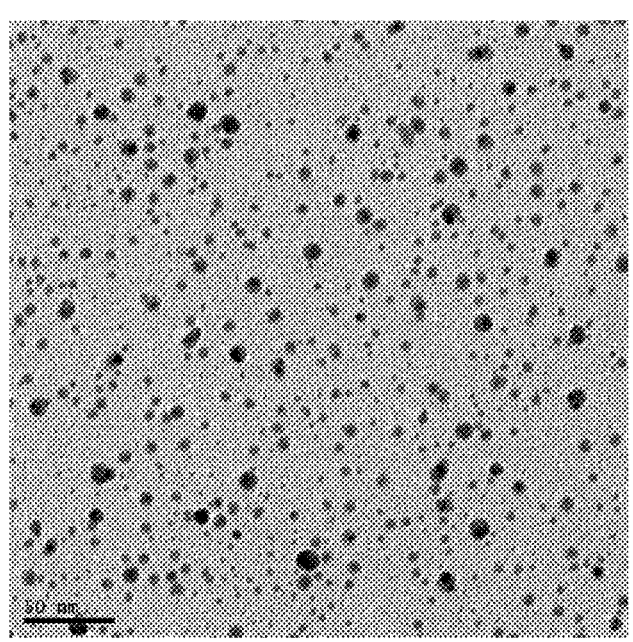

To 10 ml of 2 mM AgISt/toluene solution 0.14 g (2.8 mmol) of hydrazine monohydrate was added and dissolved therein while stirring. The reduction reaction was carried out at room temperature (25° C.) for a period of 10 minutes with stirring. The transparent solution gradually became orange and the resulting silver organosol was observed as shown in the UV-visible spectrum of FIG. 10a and the TEM image of FIG. 10b.

EXAMPLE 3

Figure 11A:
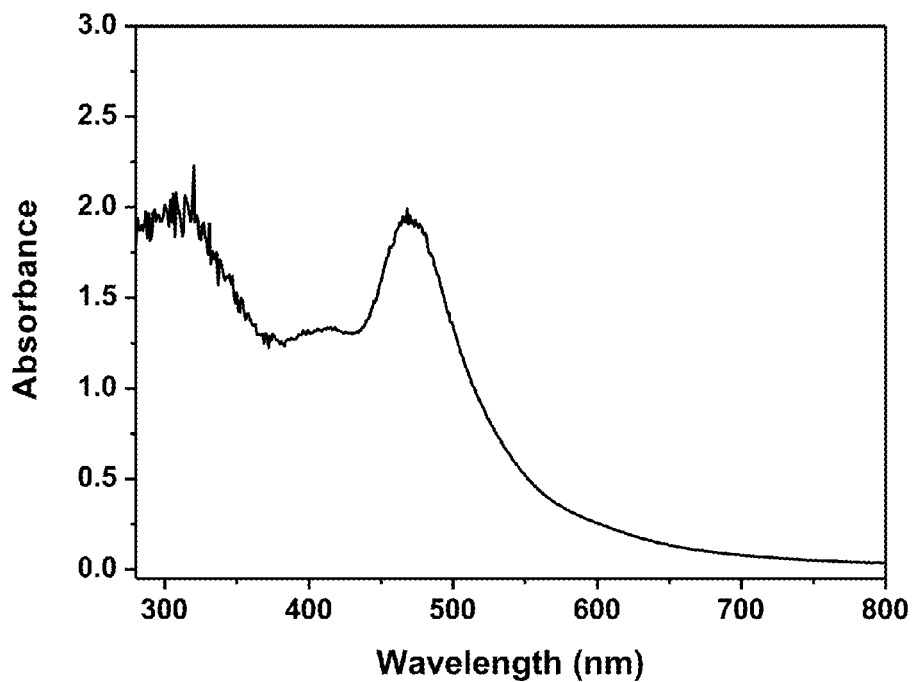
FIGS. 11a and 11b show the UV-visible spectrum and TEM image of as-prepared silver organosol using tris(trimethylsiloxy)silane as the reducing agent in Example 3.
Figure 11B:
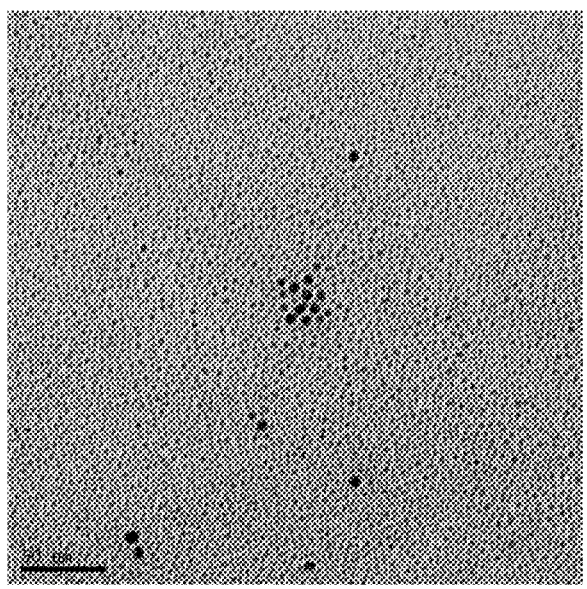

To 10 ml of 1 mM AgISt/heptane solution 0.1 g (0.34 mmol) of tris(trimethylsiloxy)silane was added and dissolved therein while stirring. The reduction reaction was carried out at room temperature (25° C.) for a period of 8 hr. The transparent solution gradually became orange and the resulting silver organosol was observed as shown in the UV-visible spectrum of FIG. 11a and the TEM image of FIG. 11b.

EXAMPLE 4

Figure 12A:
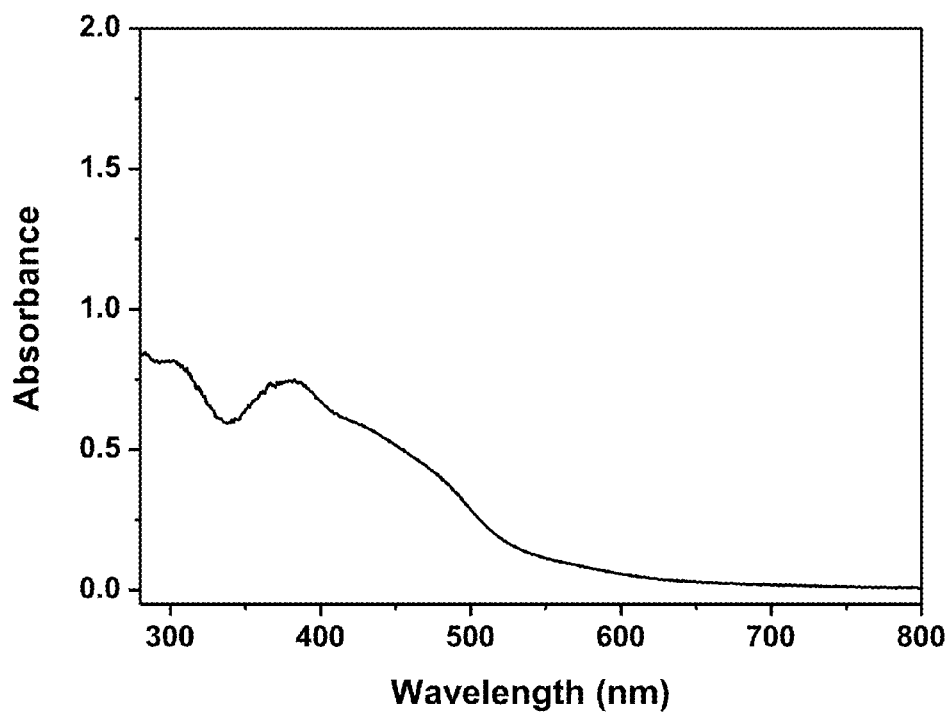
FIGS. 12a and 12b show the UV-visible spectrum and TEM image of as-prepared silver organosol using sodium borohydride ($NaBH_4$) as the reducing agent in Example 4.
Figure 12B:
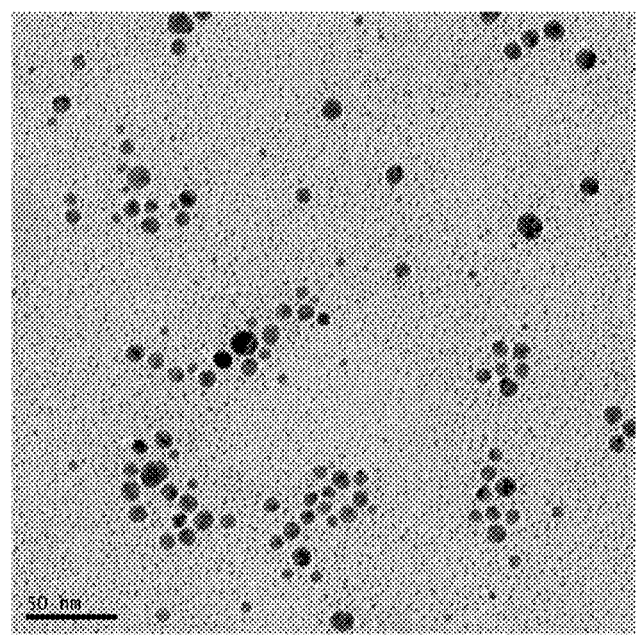

10 ml of 0.5 mM AgISt/heptane solution and 0.003 g (0.08 mmol) of sodium borohydride were mixed. The reduction reaction was carried out at 40° C. for a period of 60 minutes with stirring. The transparent solution gradually became orange and the resulting silver organosol was observed as shown in the UV-visible spectrum of FIG. 12a and the TEM image of FIG. 12b. The black precipitates (residues of $NaBH_4$) were separated from the organosol by centrifugation.

EXAMPLE 5

Synthesis of Palladium Isostearate Complex (PdISt)

PdISt was synthesized by the cation exchange reaction of sodium salt of isostearic acid and $H_2PdCl_4$ aqueous solution. 2.85 g of isostearic acid (10 mmol), 0.4 g of sodium hydroxide (10 mmol), and 100 ml triply-distilled water were well mixed at 80° C. for 30 min, then a clear solution containing sodium isostearate was formed. To this sodium isostearate solution, 100 ml of $H_2PdCl_4$ aqueous solution (50 mM) was added dropwise. The yielded waxy precipitates were collected, washed, and then dried under reduced pressure at 40° C. for 24 h.

Characterizations of PdISt

Figure 13:
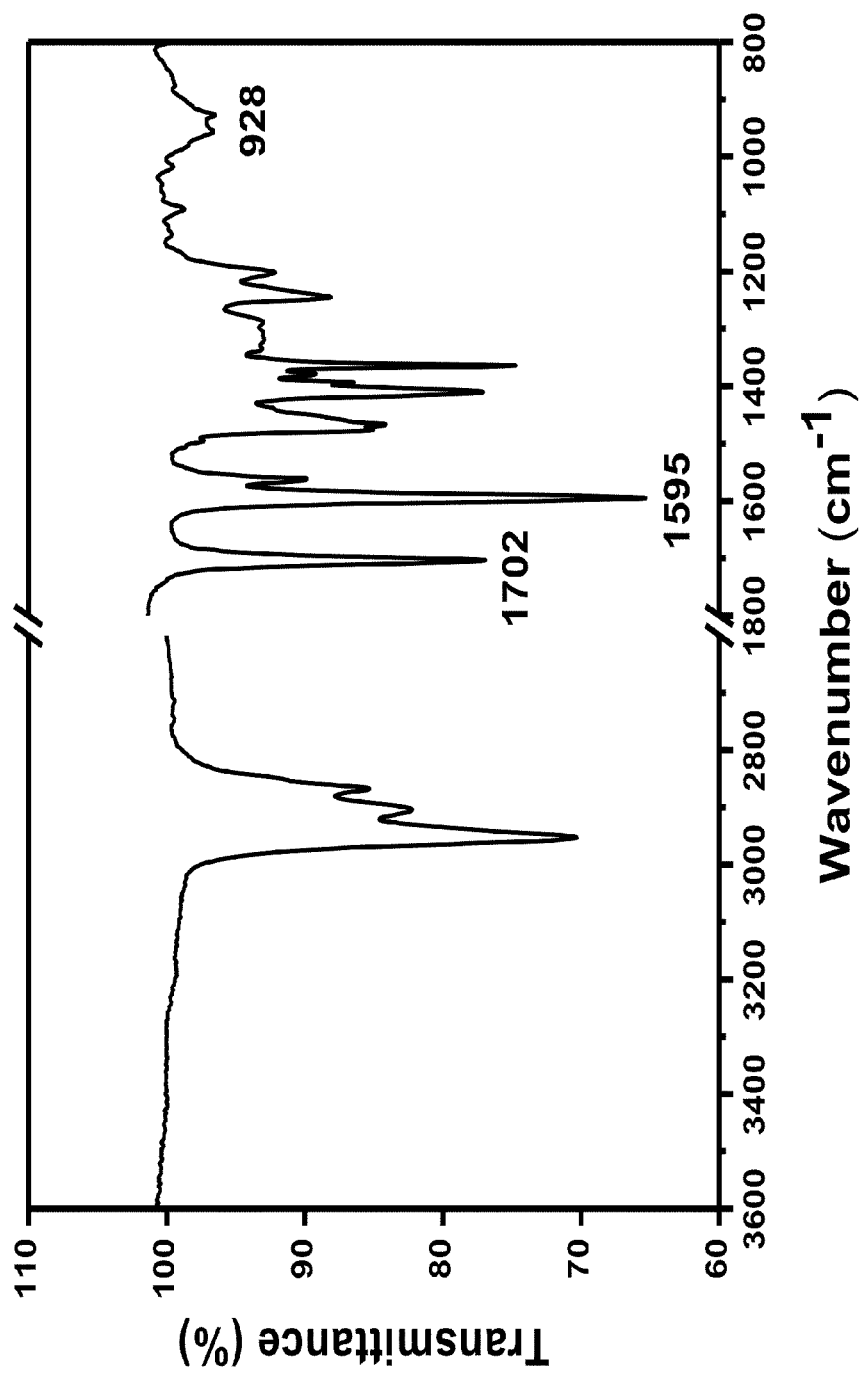
FIG. 13 shows ATR-FTIR spectrum of palladium isostearate complex (PdISt) prepared in Example 5 of the present invention.

FIG. 13 shows a FTIR spectrum of PdISt complex. The coordination between palladium cation ($Pd^{2+}$) and carboxylate anion group ($COO^-$) were appeared at 1595 $cm^{-1}$. In addition, the peaks at 1702 and 928 cm$^{-1}$ represented the C=O and out-of-plane O—H stretching bands of carboxylic acid group (COOH) were found in PdlSt complex, respectively.

Synthesis of Hydrophobic Palladium Nanoparticles (PdNPs)

A 50 ml glass vial containing 10 ml of PdlSt/oleylamine/heptane solution was placed into a 150 ml stainless steel reactor. The concentration of PdlSt and oleylamine in heptane were 0.5 mM and 5 mM, respectively. At 40° C., the reactor was filled with $H_2$ to 7 bar, followed by adding $CO_2$ to build up the total pressure of 41 bar. Through the reduction reaction, PdNPs were formed in $CO_2$-expanded heptane. After 30 min, the palladium organosol with byproducts was collected by the depressurization of $H_2/CO_2$. The byproducts were separated by centrifugal machine and the brownish palladium organosol was obtained.

Result and Discussion

Figure 14:
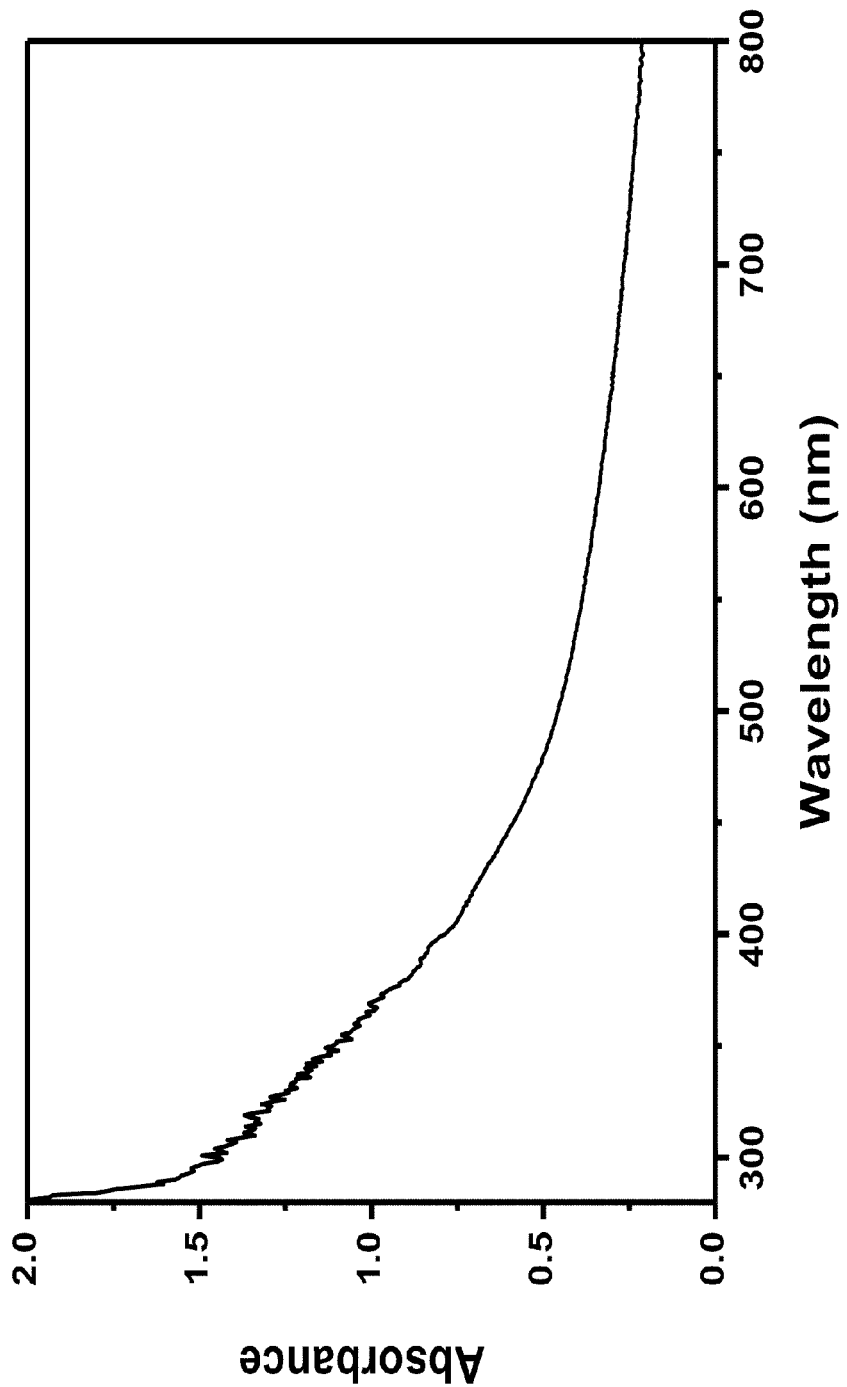
FIG. 14 show the UV-visible spectrum of as-prepared palladium organosol in Example 5.
Figure 15A:
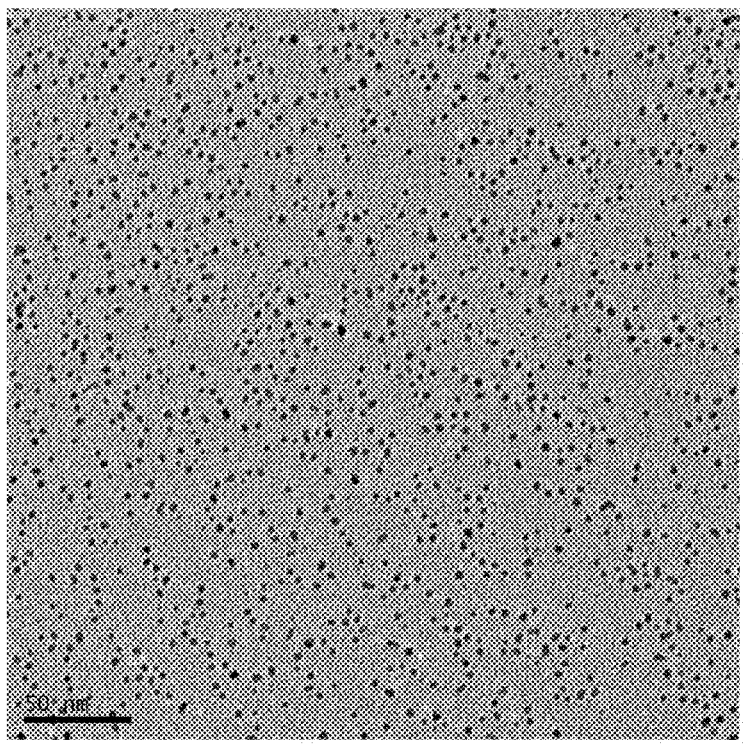
FIGS. 15a and 15b show TEM image and corresponding particle size distribution histogram of as-prepared palladium nanoparticles.
Figure 15B:
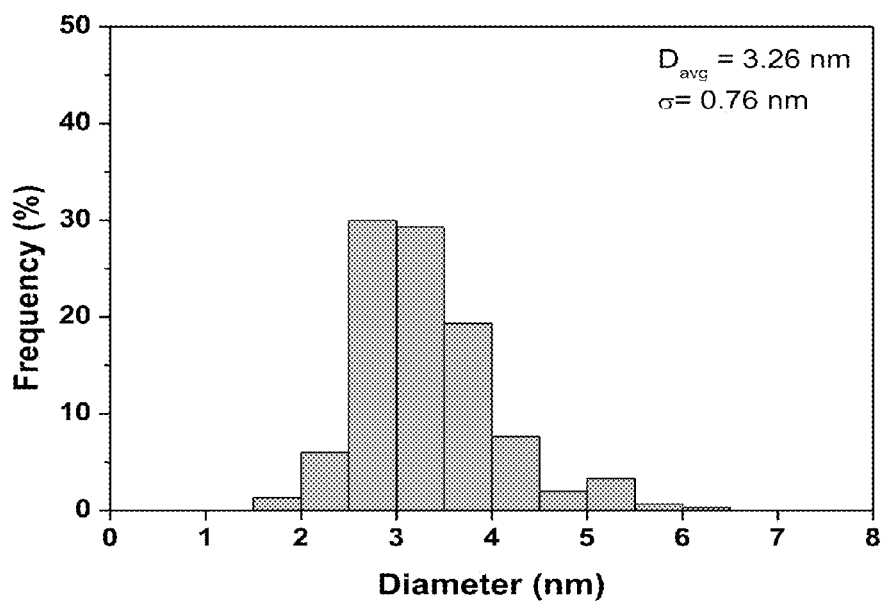

FIG. 14 shows the UV-visible absorption spectrum of PdNPs that were synthesized in $CO_2$-expanded heptane with $H_2$ at 7 bar, followed by adding $CO_2$ to build up the total pressure of 41 bar under 40° C. TEM image and the corresponding particle size distribution histograms of PdNPs are shown in FIGS. 15a and 15b, respectively. By counting 300 particles to estimate the average particle size, the average diameters of PdNPs were 3.26±0.76 nm.

The invention claimed is:

1. A method for forming metal nanoparticles comprising reducing an organometallic compound having a formula of $(R^1R^2CHCOO)_xM$ in an organic solvent, wherein x=1 or 2; M is Ag or Pd; $R^1$ and $R^2$ independently are C1-C22 linear or branched alkyl comprising a tertiary butyl group, or $R^1$ and $R^2$ together form a C10-C22 cycloalkyl comprising a tertiary butyl group.

2. The method of claim 1, wherein the organic solvent is expanded with a pressurized $CO_2$.

3. The method of claim 2, wherein the organic solvent is a non-polar organic solvent or a low polar organic solvent having a polarity less than methanol.

4. The method of claim 2, wherein the organic solvent is C4-C12 hydrocarbon, chloroform, or terahydrofuran.

5. The method of claim 2, wherein the metal precursor is reduced in an atmosphere comprising a reducing agent.

6. The method of claim 5, wherein the reducing agent is hydrogen, the atmosphere has a pressure of 1.1-275 bar, and the hydrogen has a partial pressure of 1-55 bar.

7. The method of claim 1, wherein the organic solvent is selected from the group consisting of: heptane, cycloheptane, hexane, cyclohexane, toluene, and xylene.

8. The method of claim 1, wherein M is Ag and x=1, or M is Pd and x=2.

9. The method of claim 8, wherein M is Ag and x=1.

10. The method of claim 1, wherein $R^1$ and $R^2$ independently are C3-C10 linear or branched alkyl having a terminal tertiary butyl group.

11. The method of claim 10, wherein the $(R^1R^2CHCOO)_xM$ is a metal isostearate.

12. The method of claim 1, wherein the metal precursor is reduced in an atmosphere of a reducing agent.

13. The method of claim 12, wherein the reducing agent is hydrogen, and the atmosphere has a pressure of 1 bar or higher.

14. The method of claim 1, wherein the metal precursor is reduced in the presence of a reducing agent soluble in the organic solvent.

15. The method of claim 14, the reducing agent is selected from the group consisting of: hydrazine, formaldehyde, sodium borohydride, dimethylformamide, β-D-glucose, ethylene glycol, sodium citrate, ascorbic acid, dimethyl sulfoxide, potassium bitartrate, ethanol, pyridine or poly(ethylene glycol), and tris(trimethylsiloxy)silane.

16. The method of claim 15, wherein the organic solvent is a non-polar organic solvent or a low polar organic solvent having a polarity less than methanol.

17. The method of claim 15, wherein the organic solvent is C4-C12 hydrocarbon, chloroform, or terahydrofuran.

18. The method of claim 15, wherein the organic solvent is heptane, cycloheptane, hexane, cyclohexane, toluene, xylene or a mixture thereof.

19. The method of claim 15, wherein M is Ag and x=1, M is Pd and x=2, or M is Cu and x=2.

20. The method of claim 19, wherein M is Ag and x=1.

21. The method of claim 14, wherein $R^1$ and $R^2$ independently are C6-C10 linear or branched alkyl having a terminal tertiary butyl group.

22. The method of claim 21, wherein the $(R^1R^2CHCOO)_xM$ is a metal isostearate.

23. The method of claim 1, wherein the metal precursor is reduced in the presence of a reducing agent soluble in a mixed solvent of said organic solvent and an additional solvent.

24. The method of claim 23, the reducing agent is selected from the group consisting of: hydrazine, formaldehyde, sodium borohydride, dimethylformamide, β-D-glucose, ethylene glycol, sodium citrate, ascorbic acid, dimethyl sulfoxide, potassium bitartrate, methanol, ethanol, propan-1-ol, propan-2-ol, pyridine or poly(ethylene glycol), and tris(trimethylsiloxy)silane.

25. The method of claim 24, wherein the organic solvent is a non-polar organic solvent or a low polar organic solvent having a polarity less than methanol.

26. The method of claim 24, wherein the organic solvent is C4-C12 hydrocarbon, chloroform, or terahydrofuran.

27. The method of claim 24, wherein the organic solvent is selected from the group consisting of: heptane, cycloheptane, hexane, cyclohexane, toluene, and xylene.

28. The method of claim 25, wherein the additional solvent is selected from the group consisting of: acetone, methanol, ethanol, N-methyl-2-pyrrolidone, N,N-dimethylacetamide, N,N-dimethylformamide, dimethylsulfoxide, m-cresol, pyridine, acetonitrile and 2-methoxyethanol.

29. The method of claim 24 further comprising dissolving the reducing agent in the additional solvent; dissolving the metal precursor in the organic solvent; and mixing the resulting solutions of the reducing agent and the metal precursor.

30. The method of claim 24, wherein M is Ag and x=1, or M is Pd and x=2.

31. The method of claim 24, wherein M is Ag and x=1.

32. The method of claim 23, wherein $R^1$ and $R^2$ independently are C6-C10 linear or branched alkyl having a terminal tertiary butyl group.

33. The method of claim 32, wherein the $(R^1R^2CHCOO)_xM$ is isostearate.

34. The method of claim 1, wherein the metal precursor is dissolved in the organic solvent with a concentration of 0.1-500 mM.

35. The method of claim 1, wherein an additional capping agent is added and dissolved in the organic solvent, and said additional capping agent is selected from the group consisting of: butylamine, sec-butylamine, isobutylamine, tert-butylamine, 3-methoxypropylamine, (2-methylbutyl)amine, 1,2-dimethylpropylamine, 1-ethylpropylamine, 2-aminopentane, amylamine, isopentylamine, pentylamine, tert-amylamine, 3-ethoxypropylamine, 3,3-dimethylbutylamine, hexylamine, 3-isopropoxypropylamine, heptylamine, 2-heptylamine, 1,4-dimethylpentylamine, 1,5-dimethylhexylamine, 1-methylheptylamine, 2-ethyl-1-hexylamine, octylamine, 1,1,3,3-tetramethylbutylamine, nonylamine, decylamine, dodecylamine, tridecylamine, tetradecylamine, hexadecylamine, oleylamine, octadecylamine, hexanoic acid, heptanoic acid, octanoic acid, nonanoic acid, decanoic acid, undecanoic acid, dodecanoic acid, tridecanoic acid, myristic acid, pentadecanoic acid, palmitic acid, heptadecanoic acid, stearic acid, nonadecanoic acid, arachidic acid, heneicosanoic acid, behenic acid, tricosanoic acid, lignoceric acid, pamoic acid, hexacosanoic acid, 8-methylnonanoic acid, 11-methyllauric acid, 12-methyltridecanoic acid, 12-methyltetradecanoic acid, 13-Methylmyristic acid, isopalmitic acid, 14-methylhexadecanoic acid, 15-methylpalmitic acid, 16-methylheptadecanoic acid, 17-methylstearic acid, 18-methylnonadecanoic acid, phytanic acid, 19-methylarachidic acid, and isostearic acid (2,2,4,8,10,10-Hexamethylundecane-5-carboxylic acid).

36. The method of claim 35, wherein the additional capping agent is dissolved in the organic solvent with a concentration of 0.1-5000 mM.

37. The method of claim 1, wherein the organic solvent is expanded with a pressurized inert fluid.

38. A method for forming metal nanoparticles comprising reducing an organometallic compound having a formula of $(R^1R^2CHCOO)_xM$ in an organic solvent, wherein x=1 or 2; M is Ag or Pd; $R^1$ and $R^2$ independently are C1-C22 linear or branched alkyl, or $R^1$ and $R^2$ together form a C10-C22 cycloalkyl, wherein the metal precursor is reduced in an atmosphere of a reducing agent.

39. A method for forming metal nanoparticles comprising reducing an organometallic compound having a formula of $(R^1R^2CHCOO)_xM$ in an organic solvent, wherein x=1 or 2; M is Ag or Pd; $R^1$ and $R^2$ independently are C1-C22 linear or branched alkyl, or $R^1$ and $R^2$ together form a C10-C22 cycloalkyl, wherein the organic solvent is expanded with a pressurized inert fluid.

40. The method of claim 39, wherein the pressurized inert fluid is pressurized $CO_2$.

* * * * *